(12) United States Patent  
Kilgallon et al.

(10) Patent No.: US 10,799,411 B2  
(45) Date of Patent: Oct. 13, 2020

(54) MEDICATION DISTRIBUTION PROCESS AND APPARATUS

(71) Applicant: TOUCHPOINT MEDICAL, INC., Concordville, PA (US)

(72) Inventors: James Leo Kilgallon, Wilkes-Barre, PA (US); Jeffrey C. Olson, Wilkes-Barre, PA (US)

(73) Assignee: TOUCHPOINT MEDICAL, INC., Concordville, PA (US)

( * ) Notice: Subject to any disclaimer, the term of this patent is extended or adjusted under 35 U.S.C. 154(b) by 104 days.

(21) Appl. No.: 15/128,295

(22) PCT Filed: Mar. 23, 2015

(86) PCT No.: PCT/US2015/022007  
§ 371 (c)(1),  
(2) Date: Sep. 22, 2016

(87) PCT Pub. No.: WO2015/148375  
PCT Pub. Date: Oct. 1, 2015

(65) Prior Publication Data  
US 2018/0168904 A1    Jun. 21, 2018

Related U.S. Application Data

(60) Provisional application No. 61/969,641, filed on Mar. 24, 2014.

(51) Int. Cl.  
*A61G 12/00*     (2006.01)  
*G16H 20/10*    (2018.01)  
*A61J 7/00*       (2006.01)  
*G07F 17/00*    (2006.01)  
*G06F 19/00*    (2018.01)  
*G07F 11/62*    (2006.01)

(52) U.S. Cl.  
CPC .......... *A61G 12/001* (2013.01); *A61J 7/0069* (2013.01); *G06F 19/3462* (2013.01); *G07F 17/0092* (2013.01); *G16H 20/10* (2018.01); *A61J 7/0084* (2013.01); *G07F 11/62* (2013.01)

(58) Field of Classification Search  
CPC ..... A61G 12/001; A61J 7/0069; A61J 7/0084; G07F 17/0092; G07F 11/62; G16H 20/10  
USPC ................................... 700/231–244  
See application file for complete search history.

(56) References Cited

U.S. PATENT DOCUMENTS 6,116,461 A * 9/2000 Broadfield ........... A61G 12/001  
206/443  
6,219,587 B1 * 4/2001 Ahlin .................. G06F 19/3462  
700/233

(Continued)

OTHER PUBLICATIONS

Australian Examination Report for Australian Application No. 2015236365, dated Dec. 17, 2018, 3 pages.

(Continued)

*Primary Examiner* — Michael Collins  
(74) *Attorney, Agent, or Firm* — RatnerPrestia

(57) ABSTRACT

Apparatus and process for delivering medications includes systems and methods for attaching a secure transport module that contains one or more doses of one or more medications to a docking location on a mobile system at a first location, moving the mobile system to a second location, and removing a dose of at least one of the one or more medications from the secure transport module.

41 Claims, 13 Drawing Sheets

(56) References Cited

U.S. PATENT DOCUMENTS

| | | | |
|---|---|---|---|
| 7,040,504 B2 * | 5/2006 | Broadfield | A61G 12/001 221/98 |
| 7,155,306 B2 * | 12/2006 | Haitin | A61G 12/001 700/242 |
| 7,463,947 B1 * | 12/2008 | Frederick | G07F 7/06 700/236 |
| 7,502,666 B2 * | 3/2009 | Siegel | G06F 19/3462 700/236 |
| 7,747,347 B2 * | 6/2010 | Park, IV | A61G 12/001 221/121 |
| 7,809,470 B2 * | 10/2010 | Shoenfeld | G08B 13/14 700/243 |
| 8,019,471 B2 * | 9/2011 | Bogash | G06F 19/3462 700/242 |
| 8,417,381 B2 * | 4/2013 | Vonk | A61J 7/0481 700/244 |
| 8,457,784 B2 | 6/2013 | Rahilly et al. | |
| 8,948,914 B2 * | 2/2015 | Zini | G06F 19/3462 700/258 |
| 9,600,634 B2 * | 3/2017 | Bell | A61J 7/0084 |
| 2004/0262867 A1 * | 12/2004 | Arceta | A61G 12/001 280/47.35 |
| 2007/0078562 A1 * | 4/2007 | Park, IV | A61G 12/001 700/243 |
| 2009/0037020 A1 * | 2/2009 | Brown | G07F 11/62 700/240 |
| 2009/0108016 A1 * | 4/2009 | Brown | A61J 7/0084 221/28 |
| 2009/0138122 A1 * | 5/2009 | Wagner | G07F 11/62 700/226 |
| 2010/0234995 A1 * | 9/2010 | Zini | G05B 19/41895 700/258 |
| 2014/0108028 A1 * | 4/2014 | Braun | B65G 47/04 705/2 |
| 2015/0005934 A1 * | 1/2015 | Bell | G07C 9/00309 700/237 |
| 2017/0161459 A1 * | 6/2017 | Bell | A61J 7/0084 |

OTHER PUBLICATIONS

Chinese Office Action for Chinese Application No. 201580027251.1, dated Nov. 28, 2018, with translation, 21 pages.
Australian Examination Report for Australian Application No. 2015236365, dated May 13, 2019, 3 pages.
International Search Report and Written Opinion dated Jun. 22, 2015, application No. PCT/US2015/022007.

* cited by examiner

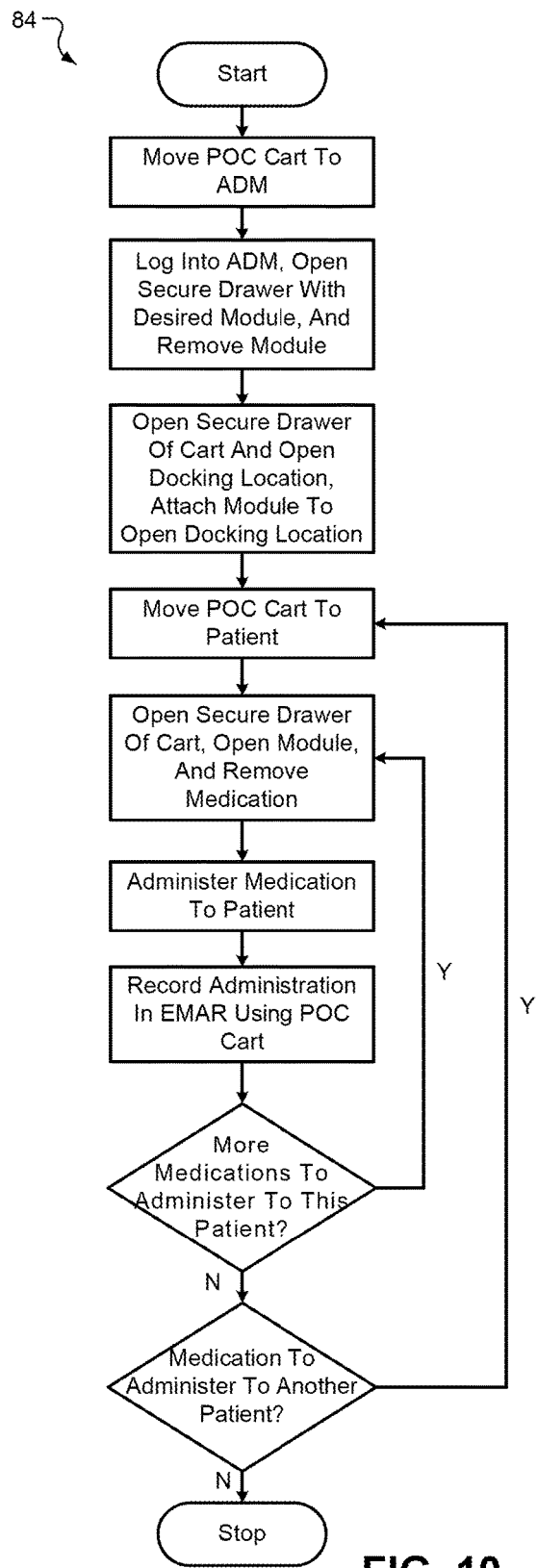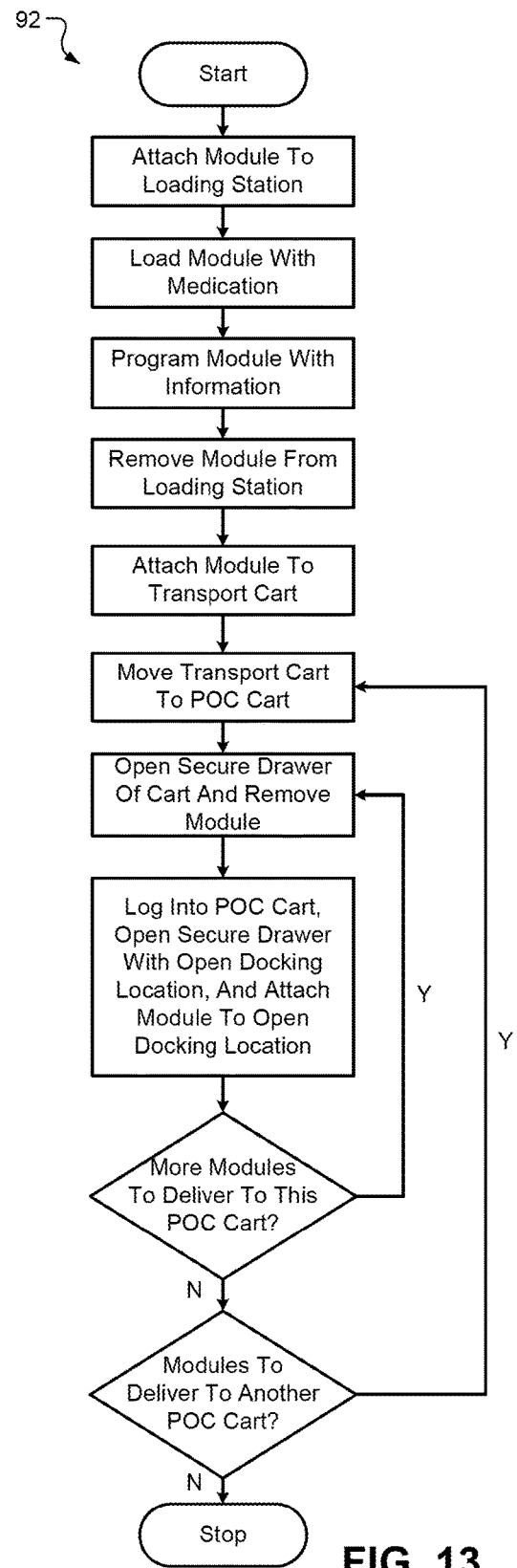
FIG. 10
FIG. 13

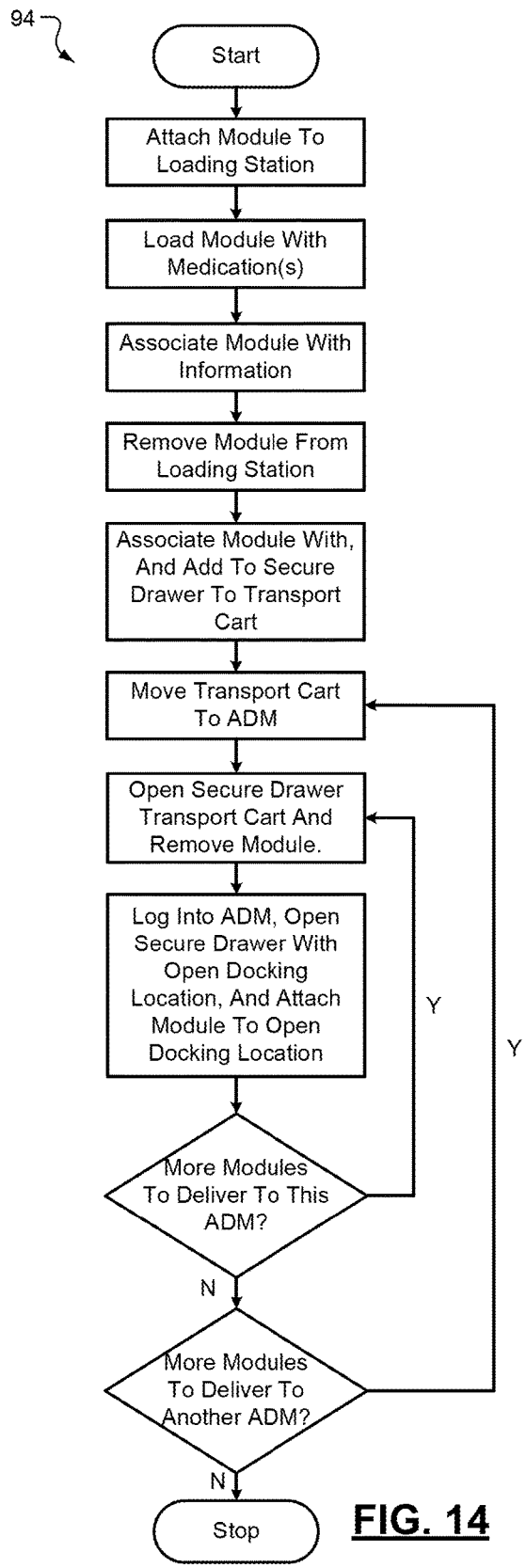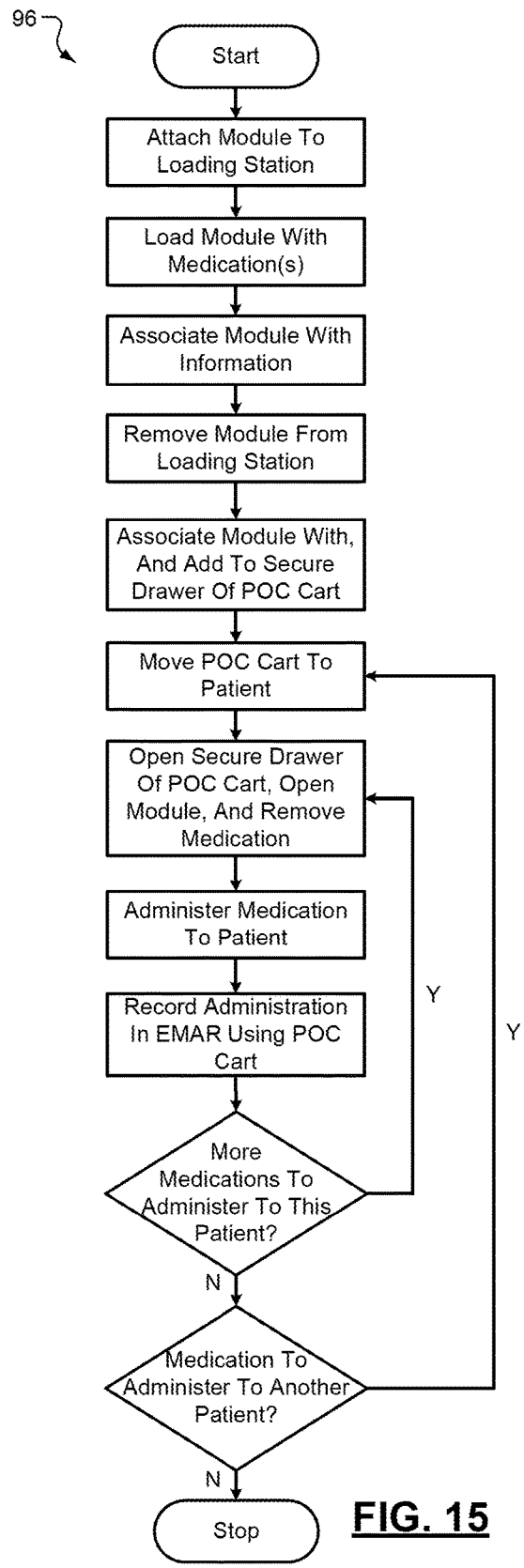
FIG. 14
FIG. 15

MEDICATION DISTRIBUTION PROCESS AND APPARATUS

CROSS REFERENCE TO RELATED APPLICATIONS

This is the U.S. National Phase application of PCT/US2015/022007, filed Mar. 23, 2015, which claims priority to U.S. Provisional Application No. 61/969,641, filed Mar. 24, 2014, the disclosures of each of these applications being incorporated herein by reference in their entireties for all purposes.

FIELD

The present disclosure relates to devices, systems and methods for tracking distribution of medications in a medical facility.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Known medication distribution systems may store medications in secure transportable compartments. The compartments may be loaded in the pharmacy and then transported as a loose item to an automated dispensing machine (ADM) and loaded into the ADM, whereupon the ADM detects the presence of the compartment and updates the system. The nurse removes medications from the compartment at the ADM and transports the medications (often in a pocket or other non-secure location) to the patient and administers the medication.

SUMMARY

The disclosure provided apparatus and process for delivering medications includes systems and methods for attaching a secure transport module that contains one or more doses of one or more medications to a docking location on a mobile system at a first location, moving the mobile system to a second location, and removing a dose of at least one of the one or more medications from the secure transport module.

In other features, the docking location is configured to prevent access to the medications contained in the secure transport module while the secure transport module is attached to the docking location. The secure transport module has an open configuration and a closed configuration and is configured to prevent access to the medications contained therein when in the closed configuration.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 10 is a flow chart of a hybrid medication distribution process according to the principles of the present disclosure;

FIG. 13 is a flow chart of an exemplary medication distribution process according to the principles of the present disclosure;

FIGS. 14-19 are additional example embodiments of methods of using a secure transportable module, also referred to as a "pod," to transport medications according to the principles of the present disclosure;

In the drawings, reference numbers may be reused to identify similar and/or identical elements.

DETAILED DESCRIPTION

Figure 1:
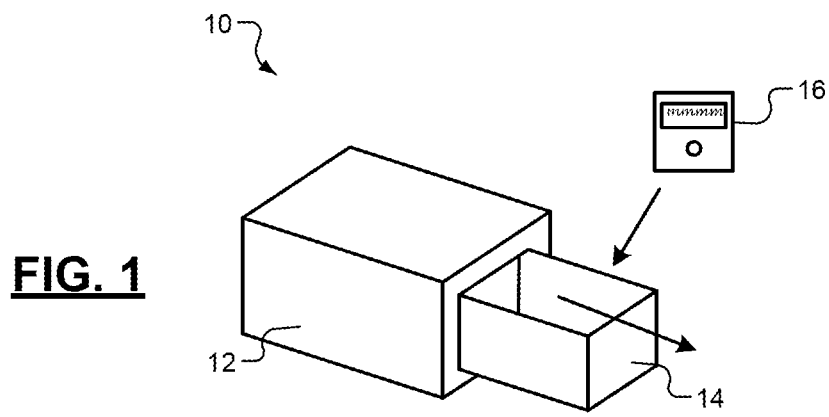
FIG. 1 depicts an exemplary embodiment of a secure transport module according to the principles of the present disclosure.

Locations of medication transport mechanisms (e.g., compartments) may be unknown after leaving the pharmacy and before loading into an automated dispensing machine (ADM). The location of the dispensed medication is unknown after removal from the ADM and before the entry of an administration record in the Electronic Medical Administration Record (EMAR). Accordingly, systems and methods according to the principles of the present disclosure relate to tracking medications in a hospital from the pharmacy to the bedside. It is desirable to know the current location of medications after a pharmacist dispenses the medication in the pharmacy until the medication is administered to a patient.

The transport of a module while attached to a "smart" transport cart or point-of-care (POC) cart according to the principles of the present disclosure allows the system to know that the module is secure, who interacted with it, and, if the cart is equipped with a real-time location system (RTLS), the physical location of the module. Attaching the module to a POC cart allows the system to know where the medication is until the medication is at the bedside. Accordingly, the present disclosure relates to systems and methods for continuously tracking the location of a medication from the time that a clinician (e.g., pharmacist) dispenses a medication in a first location (e.g., the pharmacy) until the medication is dispensed to a caregiver (e.g., a nurse) for immediate administration to a patient.

In general, the pharmacist loads one or more doses of a medication into a single secure transport module, sometimes referred to as a "pod." The module is attached to a docking location on a movable device that may be a secure storage unit on a POC cart, a transport cart, or any other movable device that has the ability to selectively retain and release the module, communicate with the module to determine at least the module identifier, and communicate with the pharmacy server. In the case of a POC cart, the medication is secured from the time the POC cart leaves the pharmacy until the nurse is at the bedside and, at the time of administration, opens the module to retrieve a dose of the medication. The medication is always securely stored and, if the POC cart is equipped with a RTLS, the exact location of the medication is always known. In the case of a transport cart, the secure transport module may be moved from the transport cart to an ADM or to another cart or to a POC cart. While this may involve additional transfers of the module between devices, the module is again always secure in a known device. There is no time period during which the module is handled as a loose item or when the medications are being handled and transported outside of the module prior to the nurse being at the bedside.

In certain embodiments, a secure transport module may be loaded with one or more medications intended for a single patient. In certain embodiments, the medications may include two or more different medications intended for a single patient. In certain embodiments, the medications may be intended for administration as a group to a single patient at the same time, for example the medications prescribed for administration as part of "the 8 o'clock med pass." In certain embodiments, the medications may include multiple individual doses of a medication, for example a 3-day supply of a prescribed medication. In certain embodiments, the medications may include a multi-dose unitary amount of medication, for example a tube of ointment containing sufficient ointment for multiple treatments. In certain embodiments, the medications may include required and optional, also known as "PRN," medications. In certain embodiments, the medications may include a device containing medication, for example an inhaler, for use by the patient or a caregiver. In certain embodiments, the module may also contain non-medication items, for example a dispensing cup or syringe.

In order to more fully describe the concepts of this disclosure, the following example of devices and processes are discussed in greater detail in the following drawings. The scope of the concept, however, is not limited to the specific details disclosed herein.

Figure 2:
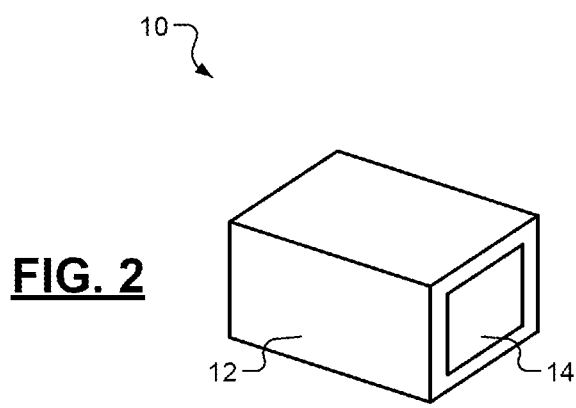
FIG. 2 depicts an exemplary embodiment of a secure transport module according to the principles of the present disclosure.

FIG. 1 and FIG. 2 depict an exemplary embodiment of a secure transport module 10. The module 10 includes an external shell 12 and an open tray 14 that slides relative to the external shell 12. In a closed configuration, shown in FIG. 2, the tray 14 is located within the external shell 12 such that the contents 16 of the tray 14 are not accessible. In an open configuration, shown in FIG. 1, the tray 14 is positioned at least partially extended from the external shell 12 such that the contents of the tray are accessible. In certain embodiments, the tray 14 moves between the closed and open positions through a linear sliding motion. In certain embodiments, the tray 14 is retained in the closed position by a retaining mechanism (not visible in FIG. 1 or 2) within the external shell 12. In certain embodiments, the external shell 12 also includes a control element (not visible in FIG. 1 or 2) that is configured to receive external commands and, upon receipt of a command, actuate the retaining mechanism to allow the tray 14 to move from the closed position toward the open position. Example operation of other transport/storage modules is described in U.S. patent application Ser. No. 13/837,164, filed on Mar. 15, 2013, which is incorporated herein by reference in its entirety.

While the examples discussed herein are drawn to the distribution and dispensing of medications in a hospital, the concepts may also be applied to the secure transport of supplies, such as implant screws or stents, or the transport of patient-specific items, for example a blood sample to be securely transported from the patient to a lab. The concepts may also be applied in non-medical environments, for example a manufacturing facility, to handle and dispense high-value components and tools.

Figure 3:
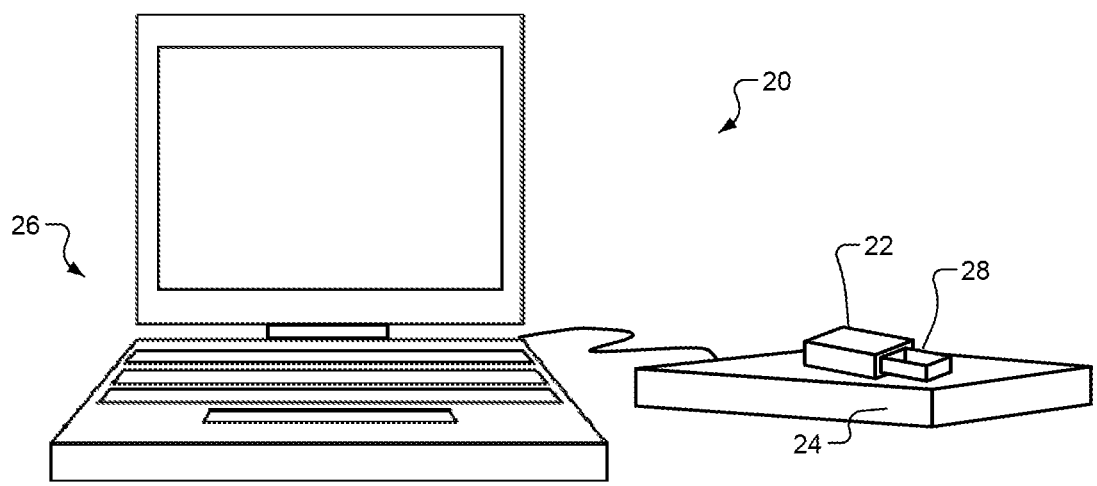
FIG. 3 depicts an exemplary loading station for a secure transport module according to the principles of the present disclosure.

FIG. 3 depicts an exemplary loading station 20 for a secure transport module 22. The module 22 is attached to a loading location 24 where the control element of the module 22 is placed in communication with a programming device 26, for example a personal computer or terminal. The terminal 26 is configured to send and receive signals with the control element, including sending a command to allow the tray 28 to move toward the open position. In certain embodiments, the module 22 includes a non-volatile memory that is coupled to the control element and configured to store instructions and information. In certain embodiments, the information may include an identifier for the module 22 that functions in much the same way as a license plate for an automobile and may be provided in a machine-readable form, for example an optically scannable barcode label or an electrically readable nonvolatile memory. In certain embodiments, the identifier may be unique within the hospital or, in other embodiments, globally unique. In certain embodiments, the memory may store information regarding a specific medication to be loaded into the module 22. This information may include one or more of a medication name, a dose, and an expiration date. In certain embodiments, the memory may store information regarding a specific patient for whom the predication is intended. This information may include one or more of a patient identifier and an administration requirement, for example a requirement to be administered with food.

Figure 4:
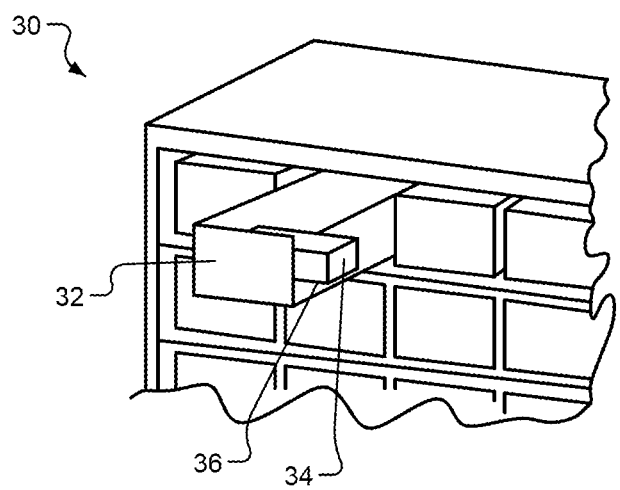
FIG. 4 illustrates a portion of an exemplary transport cart according to the principles of the present disclosure.

FIG. 4 illustrates a portion of an exemplary transport cart 30. In this example, the transport cart 30 includes a plurality of secure drawers 32, one of which is partially extended. A secure transport module 34 is attached to a docking location 36 within the secure drawer 32, with open docking positions visible on each side of the secure transport module 34.

Figure 5A:
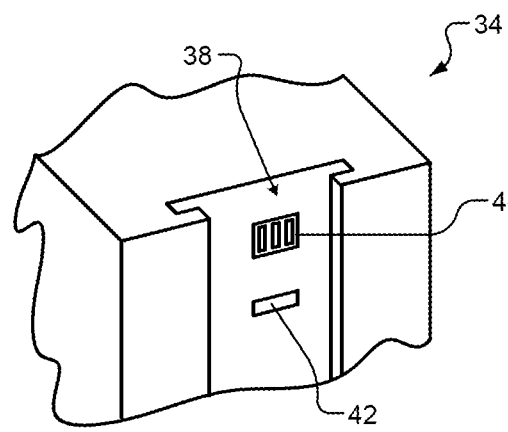
FIGS. 5A and 5B depict a portion of a secure transport module and a portion of a docking location according to the principles of the present disclosure.
Figure 5B:
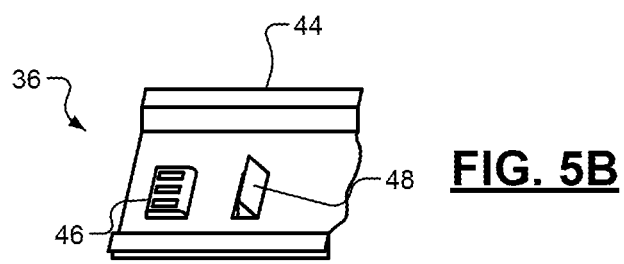

FIGS. 5A and 5B depict a portion of a secure transport module 34 and a portion of a docking location 36. In FIG. 5A, the module includes a shaped feature 38, a T-shaped slot in this example, and an electrical connector 40 that, in this example, has three contacts, and a recess 42. In FIG. 5B, the docking location 36 includes a pair of shaped rails 44 that are configured to engage the T-shaped slot 38 of the module 34 and allow sliding motion in a single direction while preventing rotation and motion in other directions. The docking location 36 includes a connector 46 configured to engage the connector 40 of the module 34 and a movable retaining mechanism 48 that, in this example, is a movable tab. The module 34 is attached to the docking location 36 by engaging the T-shaped slot 38 with the shaped rails 44 and sliding the module 34 until the movable tab 48 engages the recess 42. In certain embodiments, the tab 48 is spring-loaded and shaped to allow the body of the module 34 to displace the tab 48 downward until the recess 42 is positioned over the tab 48, whereupon the tab 48 moves upward to engage the recess 42 and prevent removal of the module 34 from the docking location 36. Other means of mechanically retaining the module 34 in the docking location 36 may be employed in place of a movable retaining mechanism 48 that is part of the docking location 36, for example a movable element attached to the module 34, without departing from the scope of this concept.

Figure 6:
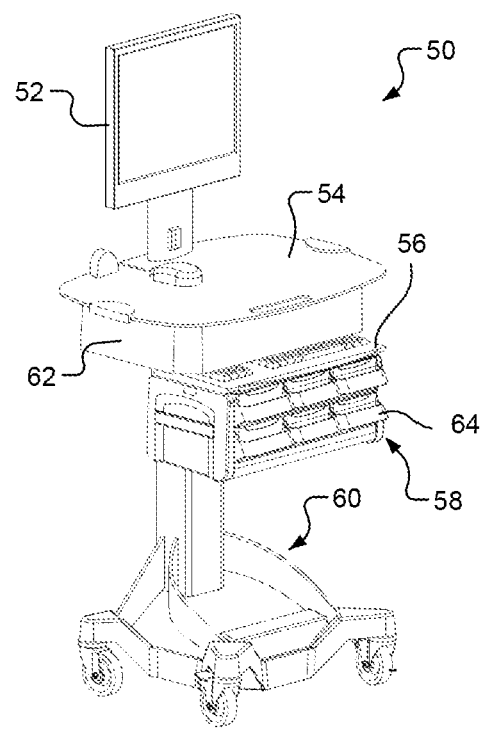
FIG. 6 is an exemplary point-of-care (POC) cart according to the principles of the present disclosure.

FIG. 6 is an exemplary point-of-care (POC) cart 50. The POC cart 50 includes a display 52, a work surface 54, a user interface 56, and a secure storage unit 58 that are all attached to a movable base 60. The POC cart 50 also includes a computer that, in certain embodiments, is contained in a storage tray 62 under the work surface 54. In certain embodiments, the computer may be provided in other locations, for example as an all-in-one (AIO) unit that includes the display 52 and is mounted in the location shown for the display 52. In certain embodiments, the computer includes a wireless communication device configured to communicate with a hospital data network. In certain embodiments, the POC cart 50 may include a RTLS device (e.g., an RFID, Wi-fi, Bluetooth, or other suitable wireless communication device) configured to provide information regarding the physical location of the POC cart 50. In certain embodiments, the secure storage unit 58 comprises one or more secure drawers 64 each having one or more docking locations configured to accept and communicate with a secure storage module in a manner similar to that described in FIGS. 5A and 5B.

Figure 7:
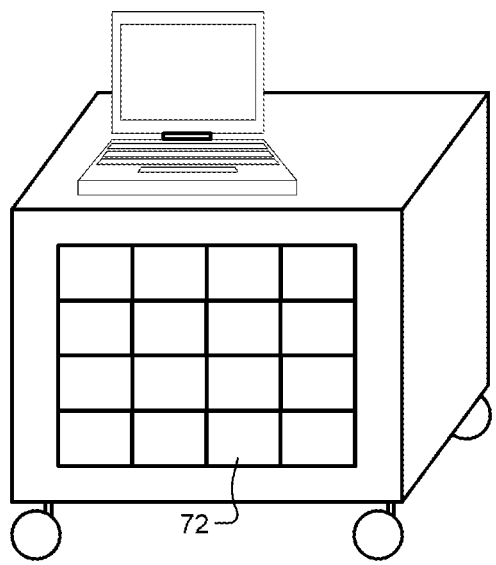
FIG. 7 is an exemplary transport cart according to the principles of the present disclosure.

FIG. 7 is an exemplary transport cart 70. The cart 70 comprises one or more secure drawers 72 each having one or more docking locations configured to accept and communicate with a secure storage module in a manner similar to that described in FIGS. 5A-5B. In certain embodiments, the cart 70 also includes a display, a user interface device, and a computer with one or more of a wireless communication device configured to communicate with a hospital data network and a RTLS device.

In certain embodiments, the docking locations of the cart 70 may be provided in locations other than within a drawer 72, for example within a cabinet having doors that prevent access to the secure transport modules when closed. In certain embodiments, the docking location may be exposed such that a secure transport module may be loaded into the docking location without a need for a secondary action, for example opening a drawer.

In certain embodiments, the secure transport module may not limit access to the contents of the module when the module is not attached to a docking location. For example, the secure transport module may be an open bin that can be retained in a docking location within a housing such that the contents are not accessible while the bin is retained in the housing. When the bin is released, the bin may be partially or completely removed from the housing such that the contents of the bin are accessible. This bin can be loaded with one or medications in the pharmacy and loaded into the housing and secured therein, thereby providing secure storage during transport between the pharmacy and a destination such as a patient bedside.

Figure 8:
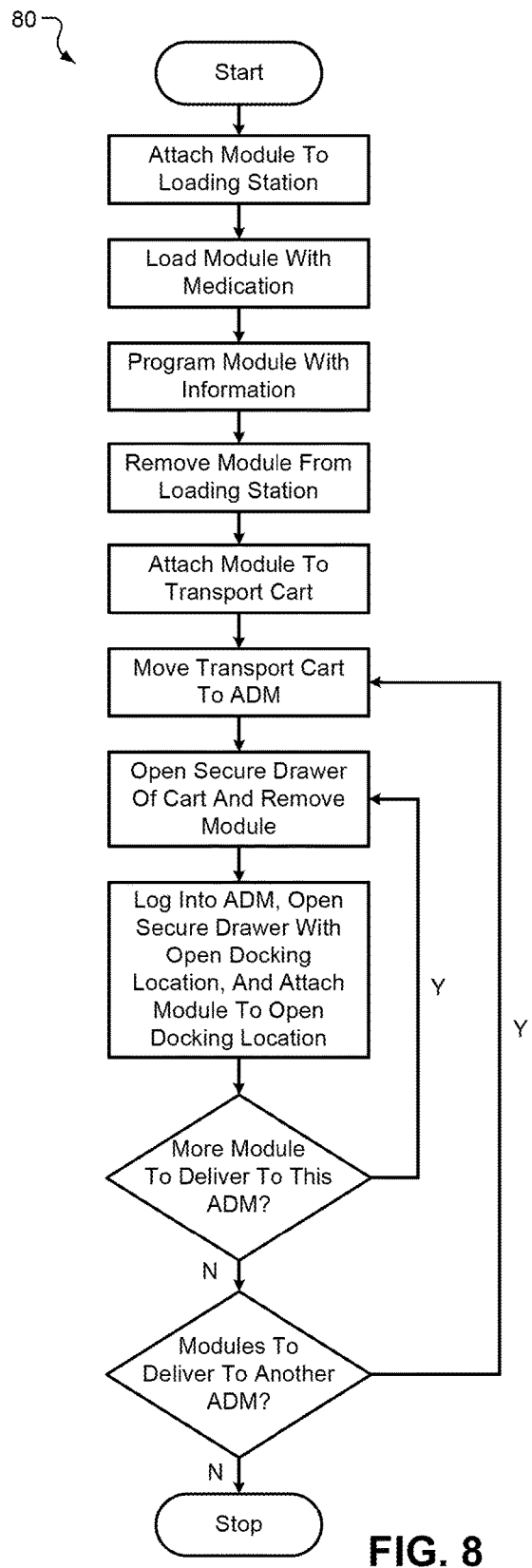
FIG. 8 is a flow chart of an exemplary medication distribution process according to the principles of the present disclosure.

FIG. 8 is a flow chart 80 of an exemplary medication distribution process. In this example, a pharmacist attaches a secure transport module, such as shown in FIG. 1, to a loading station, such as shown in FIG. 3. The pharmacist retrieves one or more doses of a medication from the pharmacy stock and loads the medication into the module. The loading station records the module identifier and information about the medication and provides this information to a server that stores the information, for example in a database, thereby "registering" the module as having a specified content.

In certain embodiments, the pharmacist may cause the loading station to store information about the medication and/or about the patient for whom the medication is intended in the memory of the module. The pharmacist then closes the module and removes the module from the loading station.

The module is attached to a transport cart, such as shown in FIG. 7. The computer on the transport cart informs the server of the receipt of the module, whereupon the server updates the location in the database.

The transport cart is moved through the hospital. In certain embodiments, the transport cart is moved to an ADM. In certain embodiments, the transport cart is moved to one of a patient room, a treatment room, an operating room, a POC cart, another transport cart, a procedural cart, or an inter-hospital transport unit.

If a secure transport module is to be moved from the transport cart to another device, the secure drawer containing the module is opened and the module released from the docking location of the drawer. In certain embodiments, the technician operating the transport cart enters information into the computer on the transport cart to indicate the module to be released and the intended destination device. In certain embodiments, the technician logs into the ADM, identifies an open docking location in the ADM, causes the drawer having the open location to open, and attaches the module to the open location. The ADM communicates with the control element of the module to retrieve information from the memory, including the module identifier and any stored information. The ADM informs the server of the receipt of the module, whereupon the server updates the location in the database.

In certain embodiments, the docking location may be behind a door or cover or may be open such that the secure transport module is exposed while docked. In certain embodiments, the docking location may not include a latching retention mechanism or may have a non-latching retention mechanism, for example a spring-loaded feature on the docking location or on the module that mates with a detent on the mating part.

In certain embodiments, the destination device may be one of a dispenser located within or mounted to a wall or door of a patient room, treatment room, or operating room. In certain embodiments, the destination device may be another transport cart, a POC cart, a procedural cart. For these destination devices, the technician operates the destination device to receive the module and the destination device informs the server of the receipt of the module. If the destination is a dispenser located proximate to a room or location associated with a patient, the transport cart will retrieve the identification of medications intended for that patient and provide an indication of which modules are to be delivered to this device. In certain embodiments, the transport cart may recognize the need for an action by means of local wireless communication, for example Bluetooth, near-field communication (NFC), radio-frequency identification (RFID), or other initiating event, for example scanning of a barcode, biometric identification of a user or patient, or manual data entry.

If there are other medications to be delivered to the same destination device, the technician repeats some of the prior steps for the additional medications.

If there are other medications to be delivered to other destination devices, the technician moves the transport cart to the next destination device and repeats some of the prior steps for the medications to be delivered to that destination device.

In certain embodiments, the transport cart may be replaced by other transportation devices, such as a hand-carried tray or a robotic transport, wherein the alternate transportation device is able to determine the identifier associated with the module and inform the server of the receipt of the module.

In certain embodiments, the transport cart includes a RTLS and, at certain times or locations, informs the server of the location of the transport cart within the hospital.

In certain embodiments, while the transport cart is located proximate to a destination device, modules may be transferred from the destination device to the transport cart. In certain embodiments, these modules may contain medications that were discontinued as part of the treatment of a patient, medications prescribed for a patient that has been moved or discharged, medications that are needed in another location, or expired medications. The modules moved from the destination device to the transport cart may be delivered to another destination device or back to the pharmacy. In certain embodiments, the path of the transport cart though the hospital may be specified to allow removal of a secure transport module containing a medication from an ADM, or other destination device, and later delivering the removed module to a different destination device. Transfer of medications between destination devices may improve a pharmacist's ability to deal with critical "stock out" situations, reduce the time to deliver a medication for a "STAT" order, adjust stock levels of medications in ADMs, or manage medication availability within the hospital.

Figure 9:
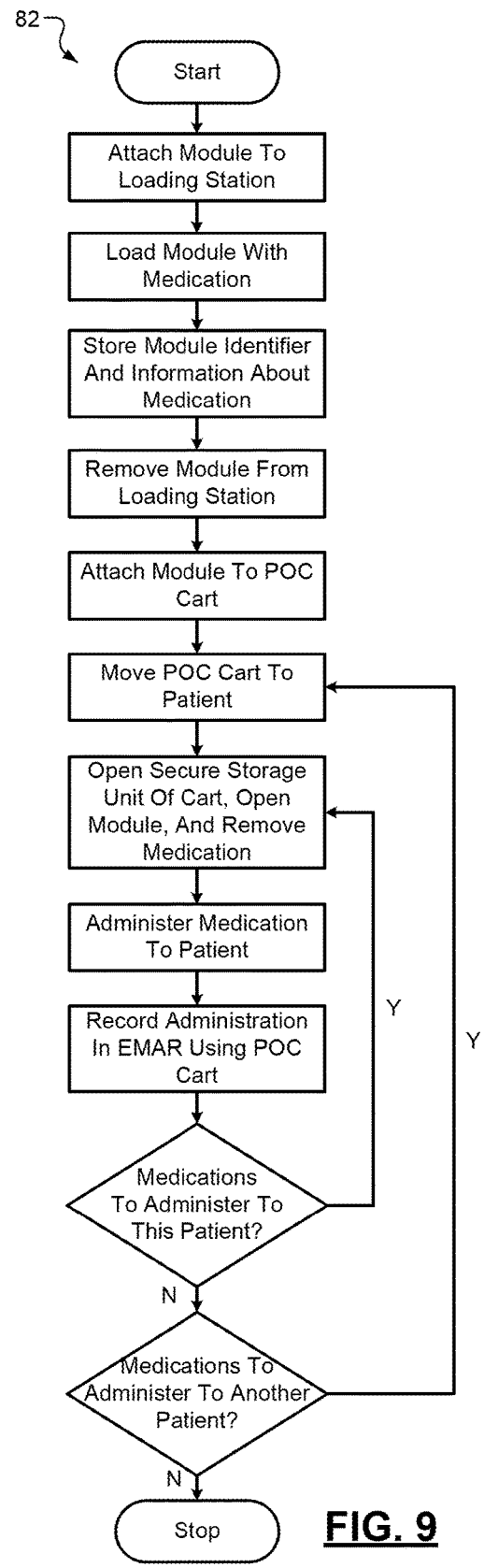
FIG. 9 is a flow chart of another medication distribution process according to the principles of the present disclosure.

FIG. 9 is a flow chart 82 of another medication distribution process. In this process, the secure transport modules are loaded and programmed as in FIG. 8. In this process, however, the modules are loaded at the pharmacy into a secure storage unit attached to a POC cart. The POC cart is then moved to a patient. As part of the medication administration process, the nurse opens the appropriate drawer of the secure storage unit, opens the module, and removes the medication from the module. The nurse administers the medication and records this administration in the Electronic Medication Administration Record (EMAR) using the computer of the POC cart. The nurse repeats the process to administer additional medications to the same patient or, in certain embodiments, dispenses multiple medications from multiple secure transport modules and then administers all the dispensed medications to the patient. The nurse then moves the POC cart to the next patient and repeats the process of dispensing and administering medications to the patient.

FIG. 10 is a flow chart 84 of a hybrid medication distribution process. Medications are loaded into secure transport modules in the pharmacy and transported to an ADM generally as described in FIG. 8. The nurse takes a POC cart to the ADM and moves the module from the ADM to the secure storage unit of the POC cart by logging into the ADM and removing the module and then attaching the module to the secure storage unit. The nurse then moves the POC cart to a patient and, as described with respect to FIG. 9, dispenses the medication from the secure transport module as part of the administration of the medication to the patient.

Figure 11:
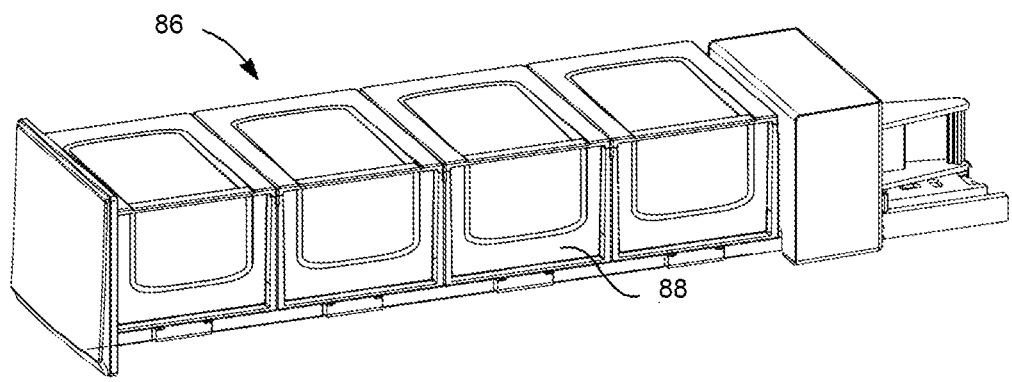
FIG. 11 is a perspective view of a cassette carrying multiple secure transport modules according to the principles of the present disclosure.

FIG. 11 is a perspective view of a cassette 86 carrying multiple secure transport modules 88. The cassette 86 can be attached to a dispensing device, for example a secure storage unit 58 as shown in FIG. 6. Use of a cassette 86 simplifies the handling of multiple modules 88 intended for a common destination or carrying multiple medications prescribed for the same patient. In certain embodiments, the cassette 86 may communicate with the dispensing device through a similar connector, shown on the right end of the cassette 86 in FIG. 11, that is similar to the connectors of FIGS. 5A-5B. In certain embodiments, the cassette 86 may also include a retention feature, similar to that shown in FIG. 5A, intended to be engaged by a retaining feature of the dispensing device that may be similar to that shown in FIG. 5B.

Figure 12:
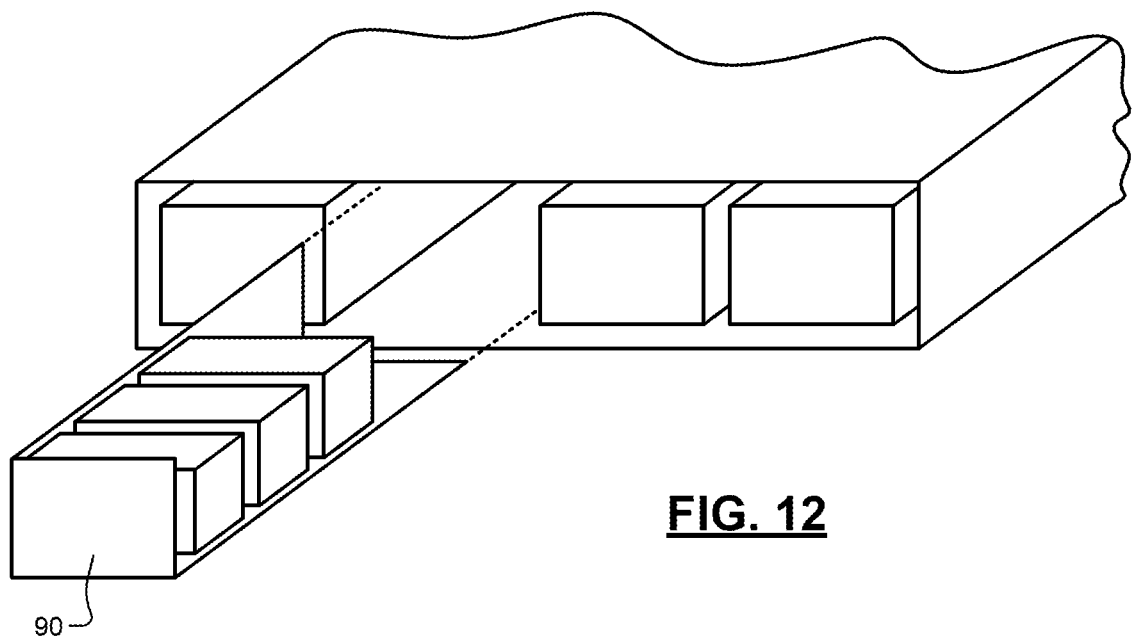
FIG. 12 depicts a removable secure drawer for a transport cart according to the principles of the present disclosure.
Figure 16:
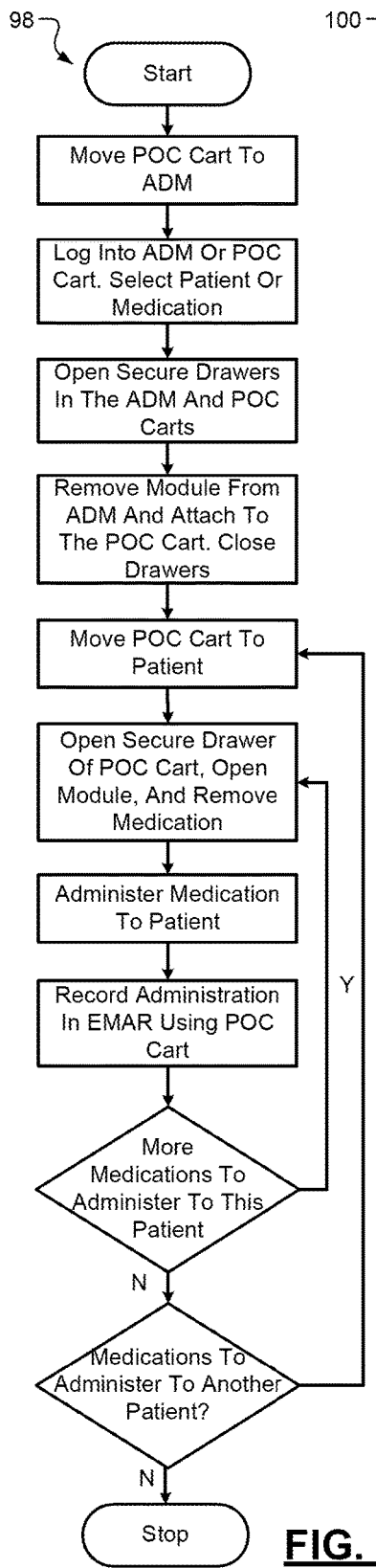
Figure 17:
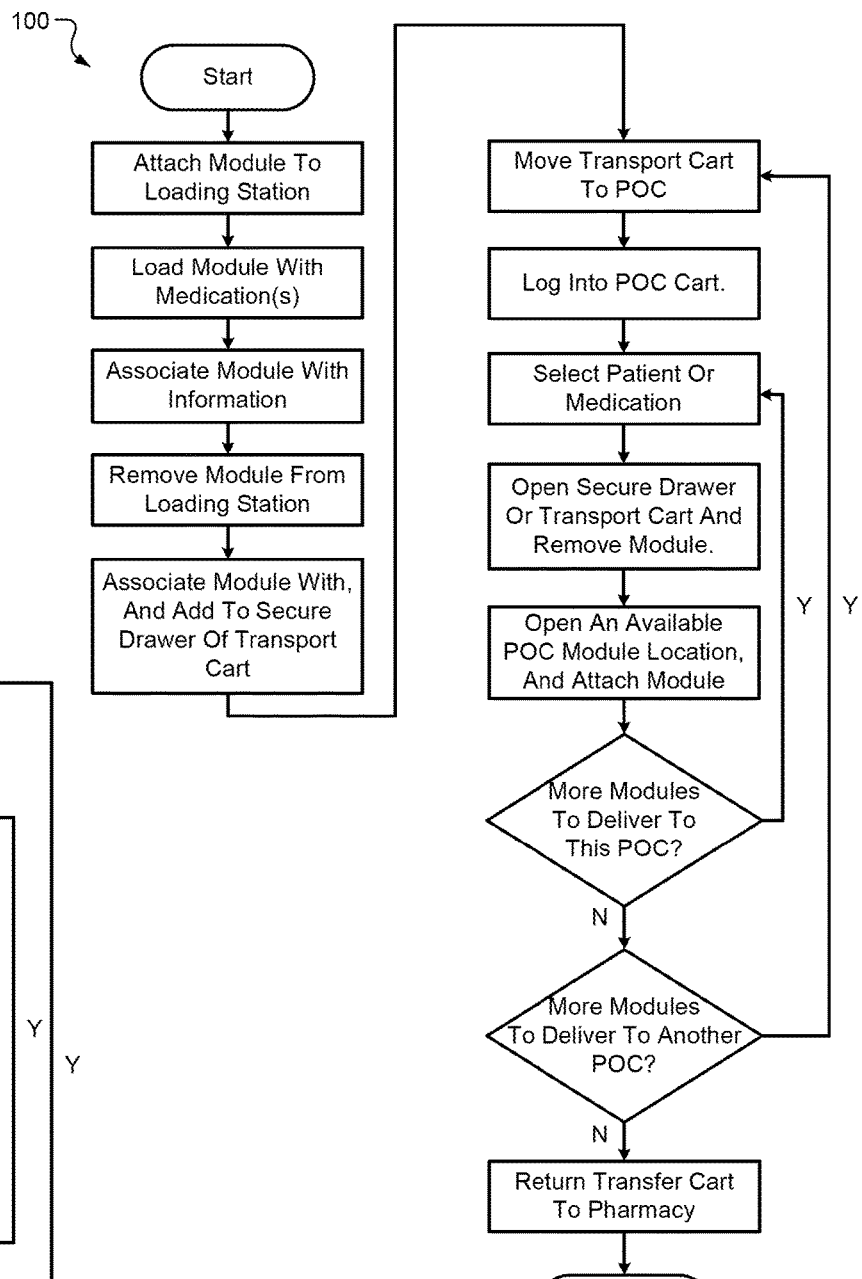
Figure 18:
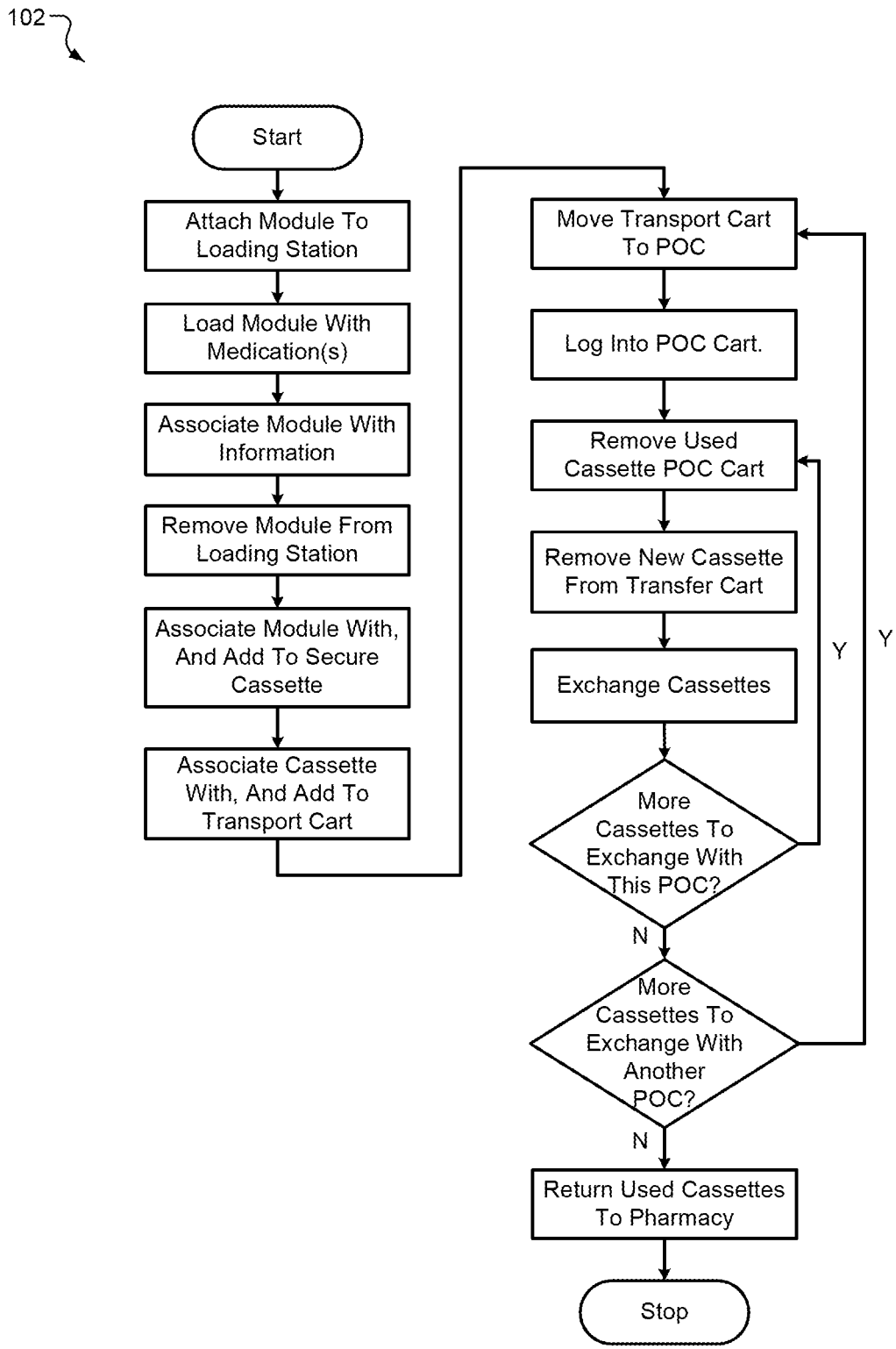
Figure 19:
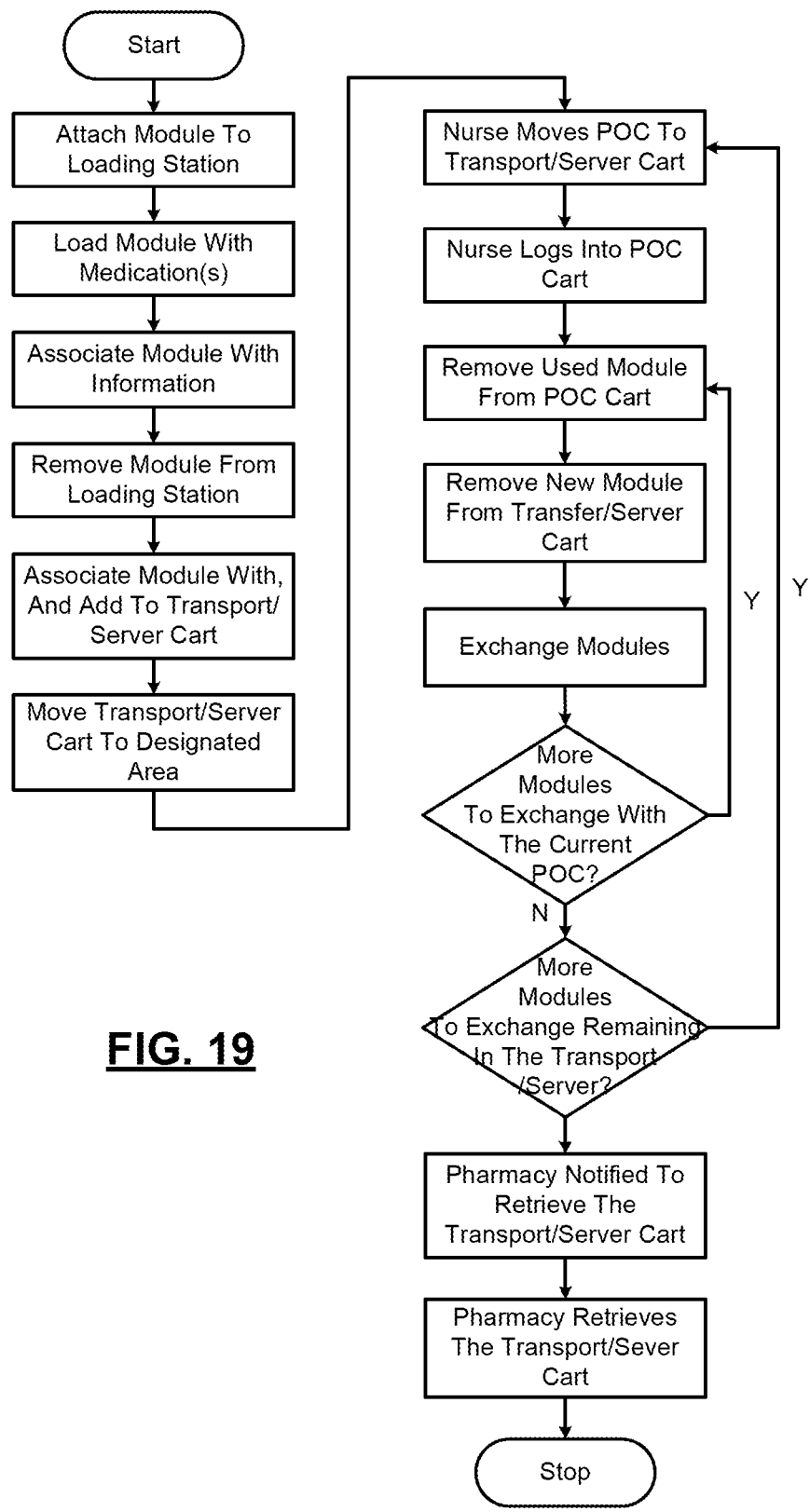

FIG. 12 depicts a removable secure drawer 90 for a transport cart. In certain embodiments, the drawer 90 is not removable in normal use and may be removed only while in a "replenishment" mode or when the transport cart is operated by a user with sufficient authority to move medications. The benefits of a revocable/replaceable drawer may be similar to those of a cassette in handling multiple modules.

FIG. 13 is a flow chart 92 of an exemplary medication distribution process. The process is largely similar to that shown in FIG. 8 with the exception that the module is transferred from the transport cart directly to a POC cart.

FIGS. 14-19 are additional example embodiments of methods 94, 96, 98, 100, 102, and 104, respectively, of using a secure transportable module, also referred to as a "pod," to transport medications.

Figure 20:
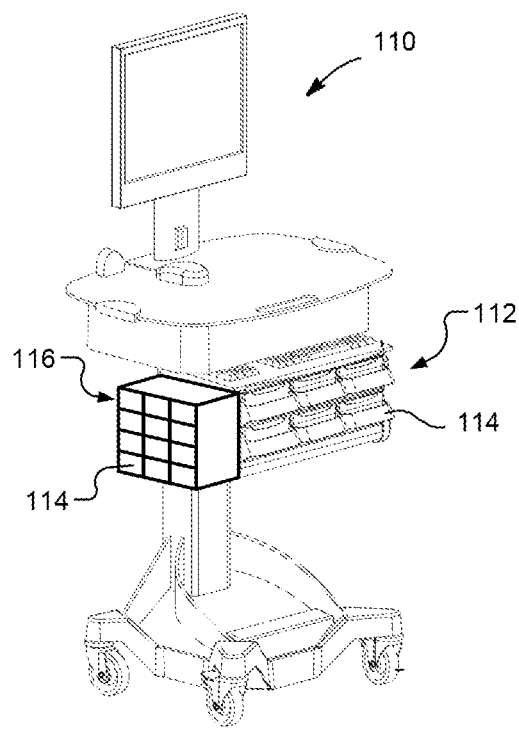
FIG. 20 is an example embodiment of a POC cart similar to the one shown in FIG. 6 according to the principles of the present disclosure.

FIG. 20 is an example embodiment of a POC cart 110 similar to the one shown in FIG. 6. In this embodiment, a secure storage unit 112 has drawers 114 that extend in multiple directions. In certain embodiments, a section of the secure storage unit 112, for example the left-side portion 116 wherein the drawers 114 extend laterally to the left in the current configuration, may rotate or move, for example the left-side portion 116 may rotate such that the drawers 114 therein are aligned in direction-of-motion with the drawers 114 of the center section.

Figure 21:
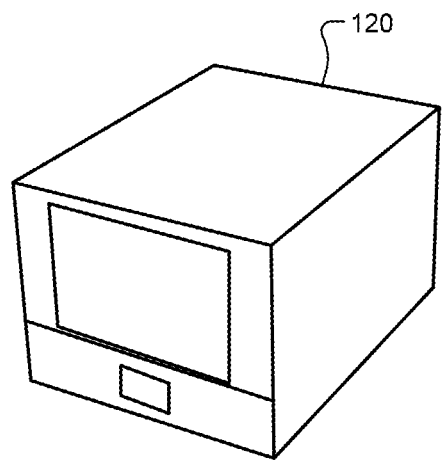
FIG. 21 is an exemplary embodiment of a secure transport module in a secure or closed configuration according to the principles of the present disclosure.

FIG. 21 is an exemplary embodiment of a secure transport module 120 in a secure or closed configuration.

Figure 22:
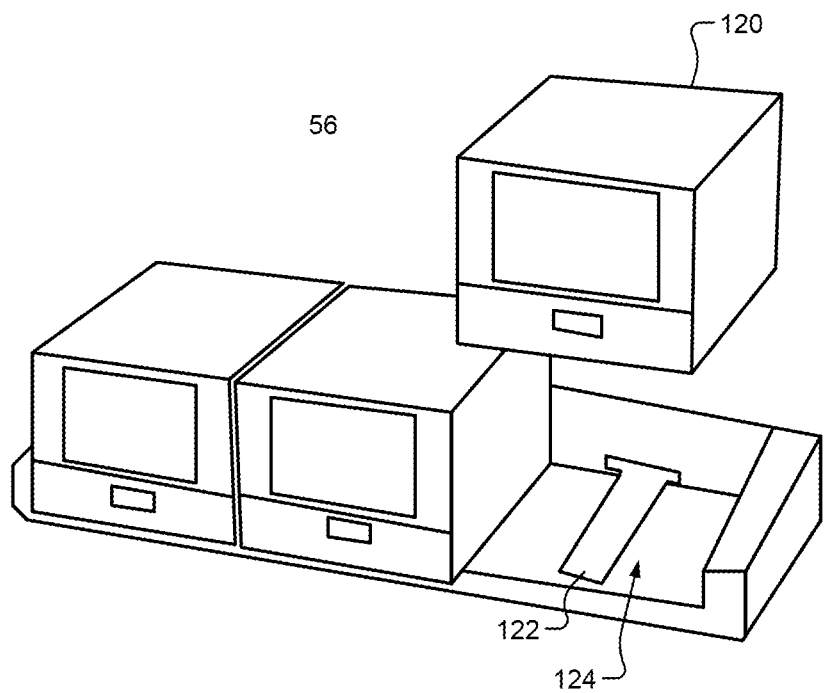
FIG. 22 depicts the secure transport module of FIG. 21 adjacent to a docking location of a tray that may, for example, be attached to a countertop according to the principles of the present disclosure.

FIG. 22 depicts the secure transport module 120 of FIG. 21 adjacent to a docking location 122 of a tray 124 that may, for example, be attached to a countertop.

Figure 23:
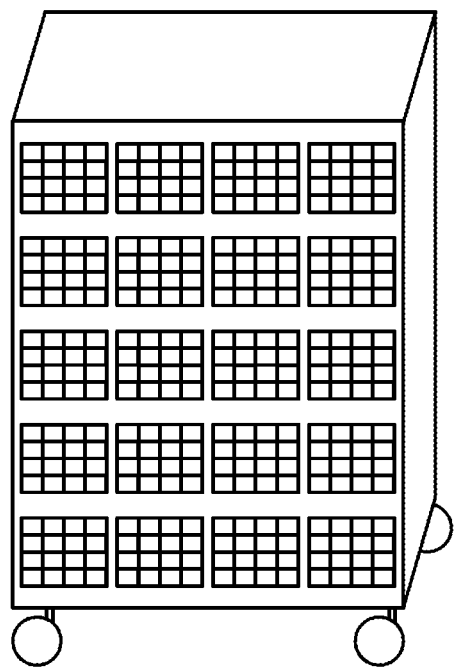
FIG. 23 is an example transport cart according to the principles of the present disclosure.

FIG. 23 is an example transport cart.

Figure 24:
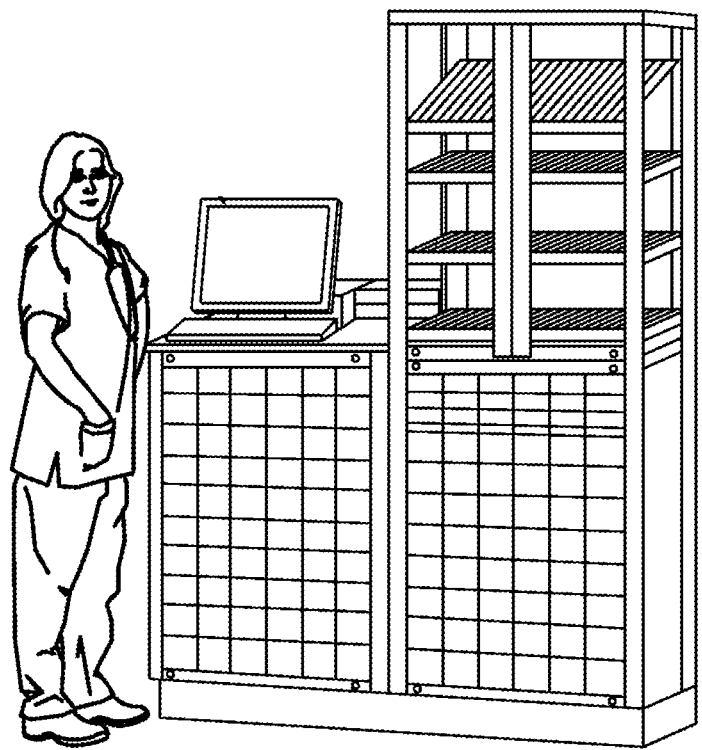
FIG. 24 is an example ADM according to the principles of the present disclosure.

FIG. 24 is an example ADM.

Figure 25:
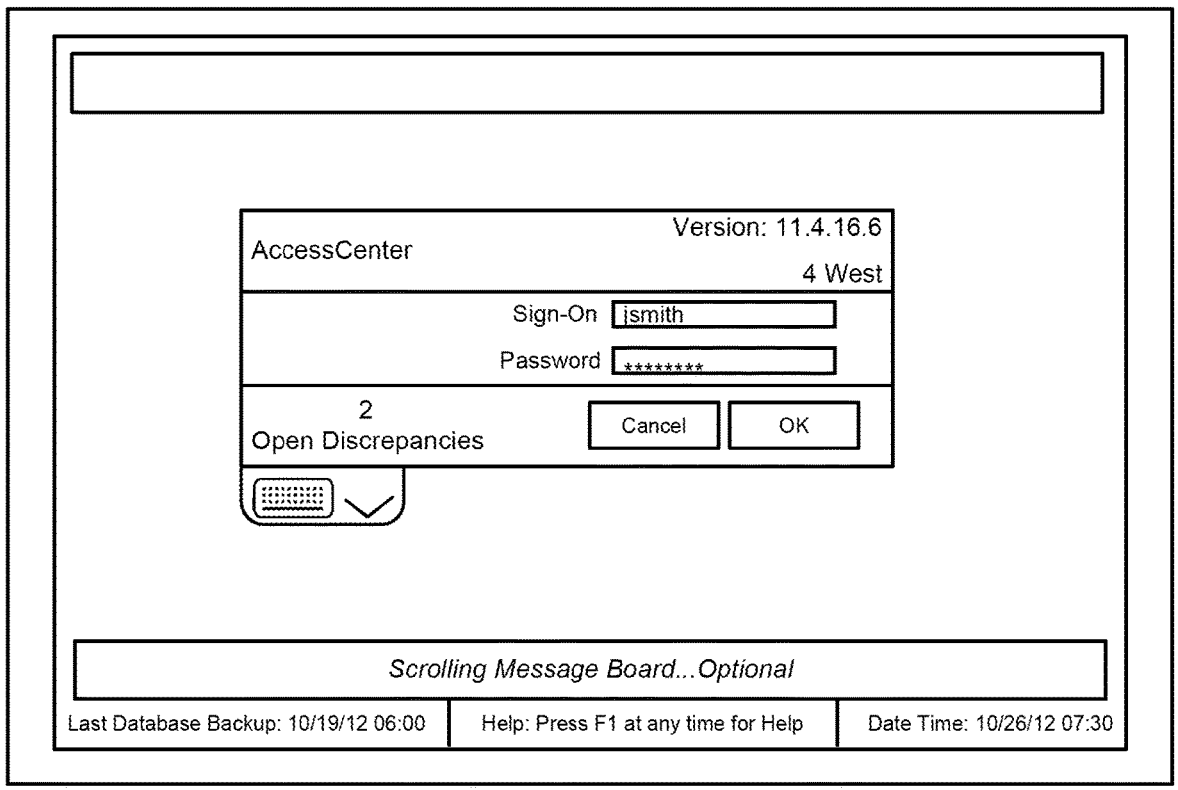
FIG. 25 is an exemplary log-in screen of the ADM of FIG. 24 according to the principles of the present disclosure.

FIG. 25 is an exemplary log-in screen of the ADM of FIG. 24.

Figure 26:
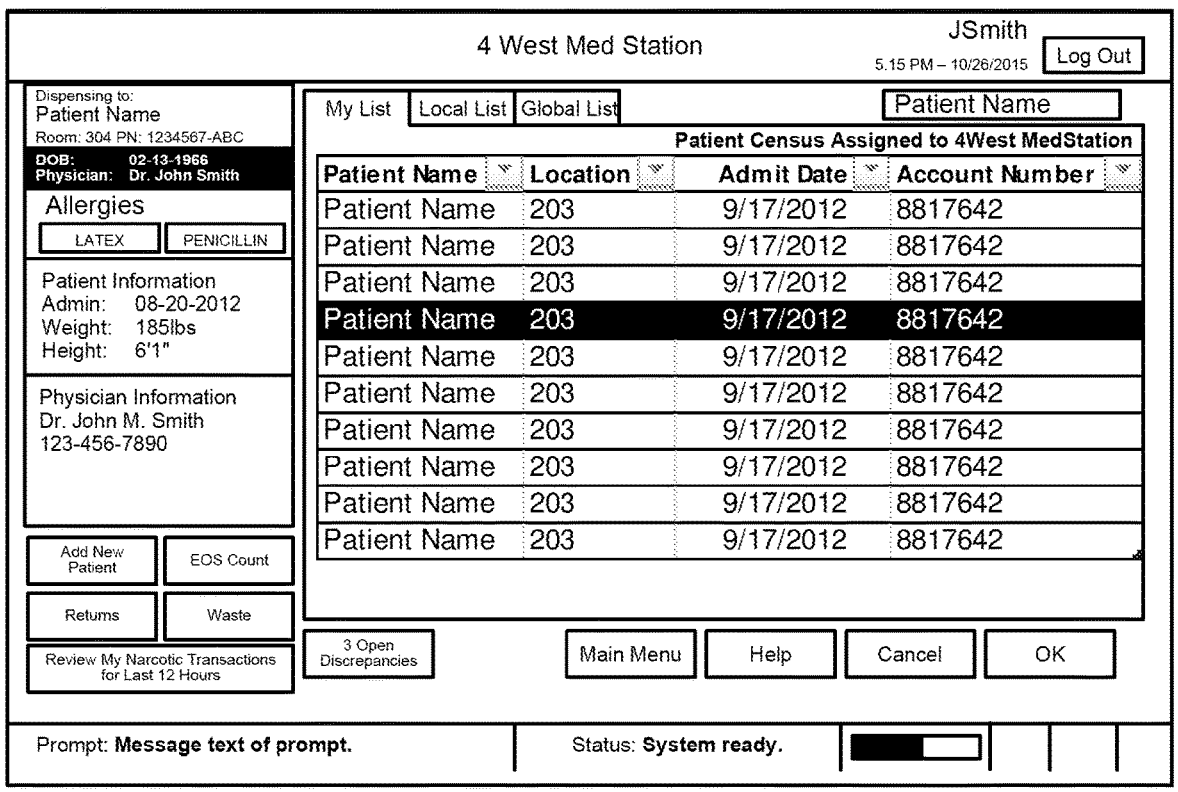
FIG. 26 is an exemplary user interface displaying information about one or more patients assigned to a specific caregiver according to the principles of the present disclosure.

FIG. 26 is an exemplary user interface displaying information about one or more patients assigned to a specific caregiver.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the control element may implement and/or communicate with a circuit, and may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. A method of delivering medications, the method comprising:
    attaching, to a loading station, a secure transport module with a memory;
    loading the secure transport module with one or more doses of one or more medications;
    programming, by the loading station, information about the medications into the memory of the secure transport module;
    communicating, to a server, a module identification unique to the secure transport module and a medication identification of the one or more doses of the one or more medications contained in the secure transport module;
    removing the secure transport module from the loading station;
    inserting the secure transport module into a docking location on a mobile system at a first location such that a first electrical connector of the secure transport module attaches to a second electrical connector of the docking location;
    in response to the first electrical connector of the secure transport module being attached to the second electrical connector of the docking location:
        communicating the module identification from the secure transport module to the docking location via the first electrical connector and the second electrical connector, and
        communicating, by the mobile system, the module identification and a mobile system identification to the server;
    moving the mobile system to a second location;
    removing the secure transport module from the docking location on the mobile system;
    attaching the secure transport module to an automated dispensing machine (ADM); and
    in response to the secure transport module being removed from the docking location on the mobile system and being attached to the ADM, communicating the secure transport module identification, the mobile system identification and an identification of the ADM to the server.

2. The method of claim 1, wherein the docking location is configured to prevent access to the one or more doses of one or more medications contained in the secure transport module while the secure transport module is attached to the docking location.

3. The method of claim 1, wherein the secure transport module has an open configuration and a dosed configuration and is configured to prevent access to the one or more doses of one or more medications contained therein when in the dosed configuration.

4. The method of claim 3, further comprising using a control element to selectively allow and prevent, in response to a command, the secure transport module to actuate from the dosed configuration to the open configuration.

5. The method of claim 4, wherein selectively allowing the secure transport module to actuate from the dosed configuration to the open configuration includes actuating a retaining mechanism in response to the command.

6. The method of claim 4, further comprising receiving the command from a programming device.

7. The method of claim 1, wherein attaching the secure transport module to the docking location includes engaging a recess of the secure transport module with a movable retaining mechanism of the docking location.

8. The method of claim 1, wherein attaching the secure transport module to the docking location includes engaging a first electrical connector of the secure transport module with a second electrical connector of the docking location.

9. The method of claim 1, wherein attaching the secure transport module to the docking station includes:
    administering the removed dose to a patient.

10. The method of claim 1,
    wherein the secure transport module is removed from the mobile system and attached to a second docking location on the mobile system or on a second mobile system, and in response to being attached to the second docking location, the mobile system or the second mobile system sends an identification of the second docking location and an identification of contents of the secure transport module to the server.

11. The method of claim 1,
wherein the secure transport module and at least one other secure transport module are removed from the mobile system and attached to different docking locations on the mobile system or on a second mobile system, and
in response to being attached to the different docking locations, the mobile system or the second mobile system sends identifications of the different docking locations and identifications of contents of the secure transport module and the at least one other secure transport module to the server.

12. A system for delivering medications, comprising:
a mobile device comprising a docking station; and
a secure transport module with a memory,
wherein the secure transport module is configured to be:
 attached to a loading station,
 loaded with one or more doses of one or more medications,
 programmed with information about the medications into the memory,
wherein the mobile device is configured to communicate, to a server, a module identification unique to the secure transport module and a medication identification of the one or more doses of the one or more medications contained in the secure transport module,
wherein the secure transport module is configured to be removed from the loading station, and inserted into the docking station at a first location such that a first electrical connector of the secure transport module attaches to a second electrical connector of the docking station,
wherein in response to the first electrical connector of the secure transport module being attached to the second electrical connector of the docking station:
 communicating the module identification from the secure transport module to the docking station via the first electrical connector and the second electrical connector, and
 communicating, by the mobile device, the module identification and a mobile device identification to the server,
wherein the mobile device is configured to move to a second location,
wherein the secure transport module has an open configuration and a closed configuration and is configured to prevent access to the one or more doses of one or more medications contained therein when in the closed configuration,
wherein the docking station is configured to prevent access to the one or more doses of one or more medications contained in the secure transport module while the secure transport module is attached to the docking station,
wherein the secure transport module is configured to be attached to an automated dispensing machine (ADM), and
wherein in response to the secure transport module being removed from the docking station on the mobile device at the second location and attached to the ADM, the mobile device is configured to communicate, the secure transport module identification, the mobile device identification and an identification of the ADM to the server.

13. The system of claim 12, wherein the secure transport module includes a control element configured to selectively allow and prevent, in response to a command, the secure transport module to actuate from the closed configuration to the open configuration.

14. The system of claim 13, wherein the secure transport module includes a retaining mechanism configured to selectively allow the secure transport module to actuate from the closed configuration to the open configuration in response to the command.

15. The system of claim 13, wherein the secure transport module is configured to receive the command from a programming device.

16. The system of claim 12, wherein the secure transport includes a recess configured to receive a movable retaining mechanism of the docking station.

17. The system of claim 16, wherein the movable retaining mechanism includes a tab.

18. The system of claim 17, wherein the tab is spring loaded.

19. The system of claim 12, wherein the secure transport module includes a first electrical connector configured to engage with a second electrical connector of the docking station.

20. The system of claim 12, wherein the secure transport module includes a T-shaped slot configured to receive a pair of rails of the docking station.

21. A system for transporting medications, the system comprising:
a secure transport module having a memory, an open configuration and a closed configuration, wherein the secure transport module is configured to be attached to a loading station and receives one or more doses of one or more medications in the open configuration and retains the one or more doses of one or more medications in the closed configuration, wherein the secure transport module is programmed with information about the medications into the memory, and wherein the secure transport module selectively transitions between the open configuration and the closed configuration in response to a control signal; and
a mobile apparatus including at least one docking station configured to receive and retain the secure transport module,
wherein the mobile apparatus is configured to communicate, to a server, a module identification of the secure transport module and a medication identification of the one or more doses of one or more medications contained in the secure transport module,
wherein the secure transport module is configured to be removed from the loading station and inserted into the docking station at a first location, such that a first electrical connector of the secure transport module attaches to a second electrical connector of the docking station,
wherein in response to the first electrical connector of the secure transport module being attached to the second electrical connector of the docking station:
 communicating the module identification from the secure transport module to the docking station via the first electrical connector and the second electrical connector, and
 communicating, by the mobile apparatus, the module identification and a mobile apparatus identification to the server,
wherein the mobile apparatus is configured to move to a second location, wherein the secure transport module has an open configuration and a dosed configuration and is configured to prevent access to the one or more doses of one or more medications contained therein when in the dosed configuration, wherein the docking station is configured to prevent access to the one or more doses of one or more medications contained in the secure transport module while the secure transport module is attached to the docking station, wherein the secure transport module is configured to be attached to an automated dispensing machine (ADM), and wherein in response to the secure transport module being removed from the docking station on the mobile apparatus at the second location and attached to the ADM, the mobile apparatus is configured to communicate, the secure transport module identification, the mobile apparatus identification and an identification of the ADM to the server.

22. The system of claim 21, further comprising:
a loading station, wherein the one or more doses of one or more medications are loaded into the secure transport module at the loading station prior to the secure transport module being loaded onto the docking station.

23. The system of claim 22, wherein the secure transport module receives a command, via the loading station, to selectively allow transitioning between the open configuration and the dosed configuration.

24. The system of claim 22, wherein the secure transport module includes memory that stores the identification of the secure transport module and/or information about the medications retained within the secure transport module.

25. The system of claim 24, wherein the loading station stores the identification of the secure transport module and/or the information about the medications and provides the identification of the secure transport module and/or the information about the medications to the remote server.

26. The system of claim 25, wherein the information about the secure transport module communicated by the mobile apparatus to the remote server includes the identification of the secure transport module and/or the information about the medications.

27. The system of claim 21, wherein the information about the secure transport module communicated by the mobile apparatus to the remote server indicates that the secure transport module has been received by the mobile apparatus.

28. The system of claim 21, wherein the information about the secure transport module communicated by the mobile apparatus to the remote server indicates a location of the secure transport module.

29. The system of claim 21, wherein the secure transport module is transferred from the mobile apparatus to an automated dispensing machine.

30. The system of claim 21, wherein the secure transport module is transitioned to the open configuration to administer the one or more doses of one or more medications to a patient.

31. A method for transporting medications, the method comprising:
attaching, to a loading station, a secure transport module with a memory;
loading one or more doses of one or more medications within the secure transport module while the secure transport module is in an open configuration;
programming, by the loading station, information about the medications into the memory of the secure transport module;
transitioning the secure transport module to a closed configuration to retain the one or more doses of one or more medications within the secure transport module and selectively allowing the secure transport module to transition to the open configuration in response to a control signal;
removing the secure transport module from the loading station;
inserting the secure transport module into a docking station of a mobile apparatus at a first location, such that a first electrical connector of the secure transport module attaches to a second electrical connector of the docking station,
wherein in response to the first electrical connector of the secure transport module being attached to the second electrical connector of the docking station:
communicating a module identification unique to the secure transport module from the secure transport module to the docking station via the first electrical connector and the second electrical connector, and
communicating, by the mobile apparatus, the module identification, a mobile apparatus identification, and a medication identification of one or more doses of one or more medications contained in the secure transport module to the server,
wherein the docking station is configured to retain the secure transport module;
moving the mobile apparatus to a second location;
removing the secure transport module from the docking station on the mobile apparatus;
attaching the secure transport module to an automated dispensing machine (ADM); and
in response to the secure transport module being removed from the docking station on the mobile apparatus and being attached to the ADM, communicating the secure transport module identification, the mobile apparatus identification and an identification of the ADM to the server.

32. The method of claim 31, further comprising:
at a loading station, loading the one or more doses of one or more medications into a secure transport module prior to the secure transport module being loaded onto the docking station.

33. The method of claim 32, further comprising, at the secure transport module, receiving a command via the loading station to selectively allow transitioning between the open configuration and the closed configuration.

34. The method of claim 32, further comprising storing, at the secure transport module, identification of the secure transport module and/or information about the medications retained within the secure transport module.

35. The method of claim 34, further comprising storing, at the loading station, the identification of the secure transport module and/or the information about the medications and providing the identification of the secure transport module and/or the information about the medications to the remote server.

36. The method of claim 35, wherein the information about the secure transport module communicated by the mobile apparatus to the remote server includes the identification of the secure transport module and/or the information about the medications.

37. The method of claim 31, wherein the information about the secure transport module communicated by the mobile apparatus to the remote server indicates that the secure transport module has been received by the mobile apparatus.

38. The method of claim 31, wherein the information about the secure transport module communicated by the mobile apparatus to the remote server indicates a location of the secure transport module.

39. The method of claim 31, further transferring the secure transport module from the mobile apparatus to an automated dispensing machine.

40. The method of claim 31, further comprising transitioning the secure transport module to the open configuration to administer the medications to a patient.

41. A method for transporting medications, the method comprising:
  attaching, to a loading station, a secure transport module with a memory;
  at the loading station, loading one or more doses of one or more medications into a secure transport module while the secure transport module is in an open configuration;
  programming, by the loading station, information about the medications into the memory of the secure transport module;
  at the loading station, transitioning the secure transport module to a dosed configuration to retain the one or more doses of one or more medications within the secure transport module; wherein the secure transport module stores a module identification unique to the secure transport module and information about the medications retained within the secure transport module;
  removing the secure transport module from the loading station and inserting the secure transport module into a docking station of a mobile apparatus at a first location, such that a first electrical connector of the secure transport module attaches to a second electrical connector of the docking station,
  wherein in response to the first electrical connector of the secure transport module being attached to the second electrical connector of the docking station:
    communicating the module identification from the secure transport module to the docking station via the first electrical connector and the second electrical connector, and
    communicating, by the mobile apparatus, the module identification, a mobile apparatus identification, and a medication identification of the one or more doses of one or more medications contained in the secure transport module to the server,
  wherein the docking station is configured to retain the secure transport module within the mobile apparatus;
  moving the mobile apparatus to a second location;
  removing the secure transport module from the docking station on the mobile apparatus;
  attaching the secure transport module to an automated dispensing machine (ADM); and
  in response to the secure transport module being removed from the docking station on the mobile apparatus and being attached to the ADM, communicating the secure transport module identification, the mobile apparatus identification and an identification of the ADM to the server.

* * * * *